United States Patent
Davenport

(10) Patent No.: US 6,237,594 B1
(45) Date of Patent: May 29, 2001

(54) PNEUMATICALLY-OPERATED GAS DEMAND APPARATUS

(75) Inventor: James M. Davenport, Fallbrook, CA (US)

(73) Assignee: Salter Labs, Arvin, CA (US)

( * ) Notice: Subject to any disclaimer, the term of this patent is extended or adjusted under 35 U.S.C. 154(b) by 0 days.

(21) Appl. No.: 09/405,420

(22) Filed: Sep. 22, 1999

(51) Int. Cl.[7] .................................................. A61M 16/00
(52) U.S. Cl. ................. 128/204.26; 128/204.23
(58) Field of Search ................. 128/204.26, 204.23, 128/205.24, 200.14, 203.12, 207.18

(56) References Cited

U.S. PATENT DOCUMENTS

| | | |
|---|---|---|
| 4,686,974 | 8/1987 | Sato et al. . |
| 5,360,000 | 11/1994 | Carter . |
| 5,584,285 | 12/1996 | Salter et al. . |
| 5,603,315 * | 2/1997 | Sasso, Jr. ........................ 128/201.18 |
| 5,666,945 | 9/1997 | Davenport . |
| 5,697,364 * | 12/1997 | Chua et al. ..................... 128/204.23 |

* cited by examiner

Primary Examiner—Glenn K. Dawson
Assistant Examiner—Teena Mitchell
(74) Attorney, Agent, or Firm—Klehr, Harrison; John F. Letchford

(57) ABSTRACT

A pneumatically-operated gas delivery device coupled in interruptible fluid communication between a recipient and at least one course of pressurized respiratory gas controls delivery of the respiratory gas to the recipient as the recipient inhales and exhales. The device includes a regulator mechanism, a supply valve and a sensing valve, wherein the supply valve delivers the respiratory gas to the recipient responsive to movement of the sensing valve. Gas flow to the supply valve is communicated from the gas source, the regulator mechanism and through a plurality of bolus chambers each of which chambers communicates a portion of the recipient's demand gas flow rate from the regulator mechanism to the supply valve. The bolus chambers allow a high-flow pulse of respiratory gas to be delivered to the patient upon initiation of inhalation coupled with steady state flow for the remainder of inhalation. Distribution of the recipient's gas flow rate among the several bolus chambers improves the dynamic performance of the device.

11 Claims, 2 Drawing Sheets

PNEUMATICALLY-OPERATED GAS DEMAND APPARATUS

CROSS-REFERENCE TO RELATED APPLICATIONS

This application is related to co-pending Application Serial No. 09/430,547, filed on Oct. 29, 1999, entitled VARIABLE PRESSURE AND FLOW CONTROL FOR A PNEUMATICALLY-OPERATED GAS DEMAND APPARATUS.

FIELD OF THE INVENTION

The present invention relates generally to respiratory equipment and, in particular, to a pneumatically-operated gas demand apparatus coupled in interruptible fluid communication between a recipient and at least one source of a pressurized gas and adapted for controlling delivery of the pressurized gas to the recipient as the recipient inhales and exhales.

BACKGROUND OF THE INVENTION

Many medical patients suffering from any one of a variety of lung ailments are often prescribed supplemental oxygen therapy so that the patient could breath oxygen-enriched air throughout the day and sometimes throughout the night. Earlier supplemental oxygen therapy employed a nasal cannula system operably connected between a tank of compressed oxygen and the patient's nose. Oxygen was continuously delivered to the patient throughout the patient's entire breathing cycle. This method of continuously delivering oxygen to the patient throughout the patient's breathing cycle was considered wasteful because much of the oxygen dissipated into the ambient air environment. Better methods of delivering oxygen to the patient were later developed which included improved equipment that would only deliver oxygen to the patient during the inhalation phase of the patient's breathing cycle. Usually, this improved equipment employed a demand valve which opened to deliver supplemental oxygen to the patient only when the patient inhaled. Numerous types of demand valves are well known in the prior art.

One such demand valve is described in U.S. Pat. No. 5,360,000 to Carter. This demand valve is compact, simplified and totally pneumatic. The demand valve which is coupled between a source of pressurized gas such as oxygen and the patient includes a valve body having a gas flow passageway and pneumatically-coupled sensing and slave diaphragms. The slave diaphragm is interposed in the gas flow passageway and prevents gas from flowing during the exhalation phase of the patient's respiratory cycle. During inhalation, which is sensed by a sensing diaphragm, the slave diaphragm moves to open the gas flow passageway, thus permitting flow of gas to the patient. Although effective in delivering gas to a patient upon demand, this demand valve has an inherent problem. When the patient inhales to cause delivery of oxygen to patient, oxygen is also vented into the ambient air environment for as long as the slave diaphragm remains opened. This leads to wastage of oxygen which is the very problem that demand valves were designed to prevent.

Furthermore, this demand valve has an inherent deficiency of delivering gas to the patient in a continuous flow stream upon and during the inhalation phase. Unfortunately, the air remaining in the patient's respiratory passageway i.e. the nasal cavity and the throat, is first taken into the lungs upon inhalation. The oxygen-enriched air then follows the remaining air and only approximately one-half of the oxygen-enriched air ever reaches the lungs. The remaining one-half of the oxygen-enriched air remains in the patient's respiratory passageway during the waning moments of inhalation and is the first to be exhaled therefrom during exhalation. It would be beneficial to the patient if this air remaining in the patient's respiratory passageway after exhalation could be purged or otherwise enriched with oxygen before it is inhaled. Such an approach is utilized in U.S. Pat. No. 4,686,974 to Sato et al.

There is a need in the industry to provide a pneumatically-operated gas demand apparatus which can control delivery of oxygen to the recipient/patient as the recipient inhales and exhales while minimizing wastage of oxygen. It would be advantageous of this pneumatically-operated gas demand apparatus can deliver a high-flow pulse of oxygen to the recipient/patient upon commencement of the inhalation phase of the patient's breathing cycle. Such a high-flow pulse of oxygen delivered upon commencement of the inhalation phase would enrich the air remaining in the patient's respiratory passageway upon inhalation and, simultaneously therewith, purge some of this air therefrom before being inhaled. It would also be advantageous if this pneumatically-operated gas demand apparatus can deliver a continuous flow of oxygen immediately after delivery of the pulse of high-flow oxygen and throughout the remaining portion of inhalation.

U.S. Pat. No. 5,666,945 to Davenport, the disclosure of which is incorporated herein by reference, describes a pneumatically-operated gas demand apparatus which overcomes many of the deficiencies of prior devices. The Davenport apparatus includes cooperating supply and sensing valves in interruptible fluid communication between a recipient (or patient) and at least a first source of pressurized gas. The supply valve includes a supply valve housing with a first diaphragm member disposed therein. Similarly, the sensing valve includes a sensing valve housing and a second diaphragm member disposed therein. The Davenport apparatus is constructed such that, when the recipient inhales, the second diaphragm member assumes a flow-causing position and the first diaphragm member assumes a flow-supplying position whereby pressurized respiratory gas is delivered to the recipient. When the recipient exhales, the second diaphragm member assumes a flow-stopping position and the first diaphragm member assumes a flow-blocking position, thereby preventing delivery of the respiratory gas to the recipient.

The pneumatically-operated gas demand apparatus of Davenport also includes a bolus chamber structure, a supply orifice element and a pilot orifice element. The bolus chamber defining a bolus chamber therein is disposed between and in fluid communication with a regulator mechanism and a supply chamber region of the supply valve. The supply orifice element having a supply orifice formed therethrough is disposed between the regulator mechanism and the bolus chamber structure. The pilot orifice element having a pilot orifice extending therethrough is disposed between a source of pressurized respiratory gas and the supply valve.

The bolus chamber functions as a repository or accumulator for a volume of pressurized respiratory gas which is discharged during inhalation and recharged during exhalation by the recipient. The bolus chamber enables the apparatus to deliver a high-flow pulse of oxygen to the recipient upon commencement of the inhalation phase of the recipient's breathing cycle. The high-flow oxygen pulse advantageously enriches the air remaining in the recipient's airway upon inhalation and, simultaneously therewith, purges some of the air from the recipient's respiratory passageway. The Davenport device also delivers a continuous flow of oxygen immediately after delivery of the pulse of high-flow oxygen and for the remaining portion of inhalation whereby the recipient receives oxygen enriched respiratory gas throughout inspiration.

The intermittent gas delivery device of Davenport may also be used with a nebulizer. Pursuant to this modality, the high-flow pulse of oxygen delivered from the bolus chamber generates a fine mist of medicament-containing aerosol within the nebulizer which is inhaled by the recipient. The mist may thereafter be followed with a flow of pressurized respiratory gas for the remainder of inhalation.

In the Davenport device, the pulse volume is proportional to the supplied flow rate. Such a system works well in circumstances where the ratio of highest to lowest recipient demand flow rate is on the order of about three to about four to one. However, many patients have rather expansive demand flow ranges. Under these circumstances, the required flow ratio (which is an empirical ratio of the maximum to minimum demand flow rates) may become quite large. The flow requirements for some recipients, for example, may range from as low as about 0.5 l pm (liters per minute) for sedentary persons to as high as about 6 l pm for persons under physical stress. This maximum to minimum flow ratio would in turn require a pressure range of up to about 12:1 or more. Such a broad band of demand flow requirements impacts design and operation of the Davenport system in several significant ways.

First, the regulator mechanism must employ a high pressure regulator to reduce the high pressure supply gas to a workable level and a low pressure regulator to service the broad range of flow and pressure delivered by the system. The high pressure regulator must be capable of supplying respiratory gas at the higher pressure regions, and the supply (or pilot) valve must be reinforced to accommodate this higher pressure. In so doing, the dynamic performance of the supply valve ("on" and "off" timing, leakage flow, and the like) may be detrimentally affected. Second, an extremely small pilot orifice must be provided between the source of pressurized respiratory gas and a control region of the supply valve to ensure proper operation of the sensing valve. Third, the operating range of the low pressure regulator must be quite broad which may result in errors in the low pressure regulator and its adjustment mechanism that may become substantial at lower operational settings.

An advantage exists, therefore, for a pneumatically-operated gas demand apparatus capable of providing a high-flow pulse of pressurized respiratory gas upon commencement of the inhalation phase of a recipient's respiratory cycle and which reliably operates in flow ranges from as low as about 0.5 l pm to as high as 6 l pm or more. The apparatus also preferably should be usable with a nebulizer to generate and deliver a medicament-containing aerosol to a recipient on demand.

OBJECTS AND SUMMARY OF THE INVENTION

An object of the present invention is to provide a pneumatically-operated gas demand apparatus for coupling in interruptible fluid communication between a recipient/patient and at least one source of pressurized respiratory gas such as oxygen. The apparatus should be operable to control delivery of oxygen or other respiratory gas to the recipient/patient as the recipient inhales and exhales while minimizing wastage of the respiratory gas.

Another object of the present invention is to provide a pneumatically-operated gas demand apparatus which can deliver one or more high-pressure boluses of oxygen to the recipient/patient upon commencement of the inhalation phase of the recipient/patient's breathing cycle and a continuous flow of oxygen thereafter and throughout the remaining period of negative pressure defining the inhalation phase of the breathing cycle.

Yet another object of the present invention is to provide a pneumatically-operated gas demand apparatus which is simple in design and compact.

A still further object of the present invention is to provide a pneumatically-operated gas demand apparatus which can be fabricated from readily available components or can be integrated into a unitary construction.

Accordingly, a pneumatically-operated gas demand apparatus of the present invention is hereinafter described. The pneumatically-operated gas demand apparatus is coupled in interruptible fluid communication between a recipient (or patient) and a first source of a pressurized first gas and is adapted for controlling delivery of the first gas to the recipient as the recipient inhales and exhales. In its broadest form, the pneumatically-operated gas demand apparatus, like that disclosed in U.S. Pat. No. 5,666,945 to Davenport, includes a supply valve and a sensing valve. The supply valve includes a supply valve housing and a flexible first diaphragm member. The supply valve housing defines a first interior chamber formed therein. The first diaphragm member is disposed within the first interior chamber and is connected to the supply valve housing in a manner to divide the first interior chamber into a supply chamber region and a control chamber region. The supply chamber region is in interruptible fluid communication with and between the first source of the first gas and the recipient and the control chamber region is in continuous fluid communication with either the first source of pressurized gas or a second source of a pressurized second gas. The first diaphragm member is operative to hermetically seal the supply chamber region and the control chamber region from one another and is operative to move between a flow-blocking position and a flow-supplying position.

The sensing valve includes a sensing valve housing and a flexible second diaphragm member. The sensing valve housing defines a second interior chamber formed therein. The second diaphragm member is disposed within the second interior chamber and is connected to the sensing valve housing in a manner to divide the second interior chamber into a venting chamber region and a sensing chamber region. The venting chamber region is in interruptible fluid communication with and between the control chamber region of the first interior chamber of the supply valve and an ambient air environment and the sensing chamber region is in continuous fluid communication with the recipient. The second diaphragm member is operative to hermetically seal the venting chamber region and the sensing chamber region from one another and is responsive, when the recipient inhales and exhales, to move between a flow-stopping position and a flow-causing position. When the recipient inhales, the second diaphragm member is in the flow-causing position thereby causing either pressurized first gas or second gas to flow from the control chamber region, through the venting chamber region and into the ambient air environment which, in turn, causes the first diaphragm member to be in the flow-supplying position thereby delivering the first gas from the first source of pressurized first gas to the recipient. When the recipient exhales, the second diaphragm member is in the flow-stopping position thereby preventing gas flow from the control chamber region, through the venting chamber region and into the ambient air environment which, in turn, causes the first diaphragm member to be in the flow-blocking position thereby preventing delivery of the first gas to the recipient.

The pneumatically-operated gas demand apparatus includes a regulator mechanism disposed between and in interruptible fluid communication with the first source of the first gas and the supply chamber region of the supply valve. The regulator mechanism, like that disclosed in U.S. Pat. No. 5,666,945 to Davenport, can be adjusted and preferably comprises a regulator housing, a flexible regulator diaphragm and a valve assembly. The regulator housing defines a regulator chamber therein. The regulator diaphragm is disposed within the regulator chamber and is connected to the regulator housing in a manner to divide the regulator chamber into a vented regulator chamber region which is in continuous fluid communication with the ambient air environment and a supply regulator chamber region which is in interruptible fluid communication between the first source of pressurized first gas and the supply chamber region of the supply valve. The regulator diaphragm is operative to hermetically seal the vented regulator chamber region and the supply regulator chamber region from one another.

The valve assembly is operably connected to the regulator diaphragm and is disposed within the supply regulator chamber region. The valve assembly is operative between a closed condition and an opened condition. In the closed condition, an upstream portion of the supply regulator chamber region is in fluid isolation with a downstream portion of the supply regulator chamber region. In the opened condition, the upstream portion of the supply regulator chamber region is in fluid communication with the downstream portion of the supply regulator chamber region. The valve assembly is resiliently and yieldably biased against the regulator diaphragm in the closed condition and the regulator diaphragm is resiliently and yieldably biased against the valve assembly in the opened condition. When a first gas pressure of the first gas reaches a threshold gas pressure amount in the downstream portion of the supply regulator chamber region, the valve assembly is in the closed condition. When the first gas pressure is less than the threshold gas pressure amount, the valve assembly is in the opened condition.

The pneumatically-operated gas demand apparatus also includes a multiple bolus chamber structure, a plurality of supply orifice elements and a pilot orifice element. The bolus chamber defining a plurality of bolus chambers therein is disposed between and in fluid communication with the regulator mechanism and the supply chamber region of the supply valve. The bolus chamber structure includes first and second supply orifice elements having first and second supply orifices formed therethrough that are respectively disposed between the regulator mechanism and the first and second bolus chambers. The pilot orifice element having a pilot orifice extending therethrough is disposed between the source of pressurized second gas and the control chamber region of the supply valve. The supply orifices and the pilot orifice can be either fixed in size or an adjustably variable in size.

Pursuant to a first preferred embodiment the dual bolus chamber construction operates to distribute the flow range of the apparatus between the first and second bolus chambers. This division of flow requirements provides an arrangement whereby even broad recipient demand flow ranges, e.g., about 0.5 l pm to 6 l pm or more, may be easily accommodated without negatively impacting the performance of the supply valve, the sensing valve or the regulator mechanism.

Preferably, when a plurality of pressurized gases are conveyed by the apparatus, the first gas and the second gas are oxygen and, therefore, the first gas and the second gas are the same. With the first and second gases being the same, the at least one gas source may comprise a first source and a second source of pressurized gas that could also, but not necessarily, be the same. The first gas and the second gas can be different from each other. If so, the first source and the second source must also be different from one another. The first gas and the second gas are selected from either different ones or the same one of a group of gases consisting of oxygen, nitrous oxide, air and other types of gases.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE EXEMPLARY EMBODIMENTS

A pneumatically-operated gas demand apparatus is coupled in interruptible fluid communication between a recipient and a source of pressurized oxygen and is adapted for controlling delivery of oxygen to the recipient as the recipient inhales and exhales. Although the pneumatically-operated gas demand apparatus is specifically suited to provide oxygen to a recipient/patient, one of ordinary skill in the art would appreciate that the present invention can also be adapted and used to deliver other kinds of gases to recipients such as nitrous oxide. Further, since the pneumatically-operated gas demand apparatus can deliver and operate with either a single gas such as oxygen or two gases such as oxygen and inexpensive compressed air, other types of gases can also be employed without departing from the spirit and concepts of the present invention.

Figure 1:
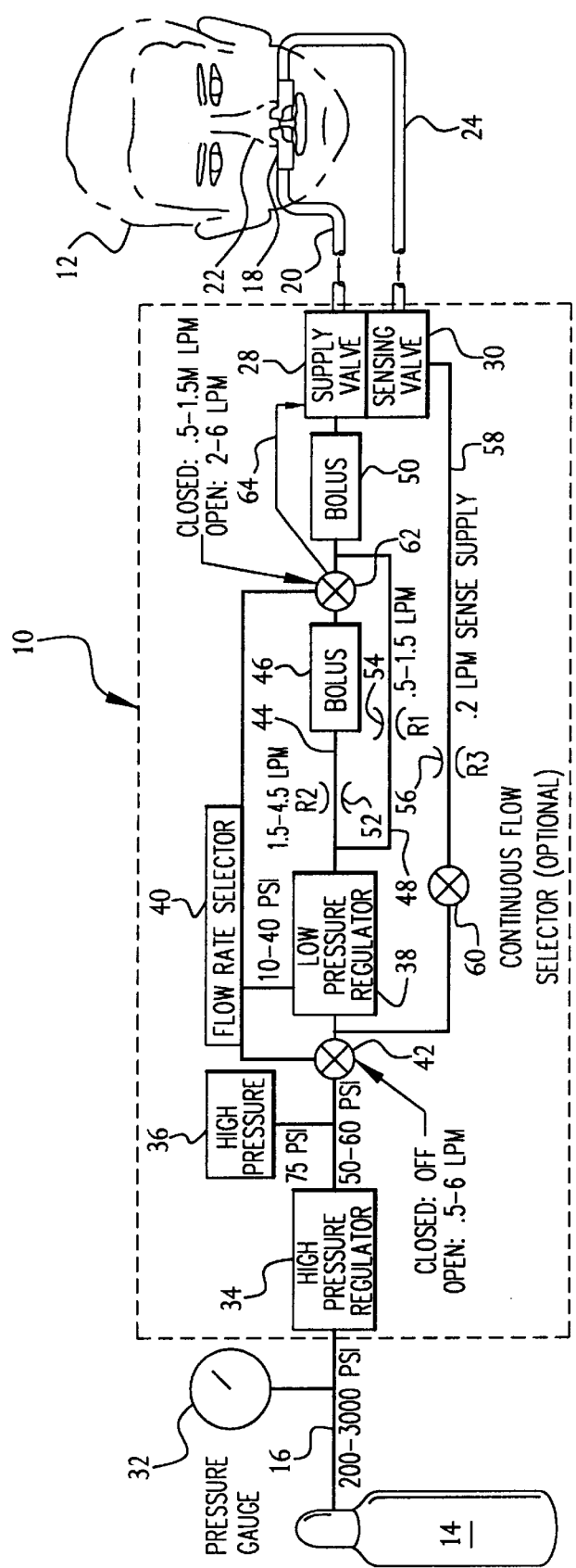
FIG. 1 is a schematic diagram of a pneumatically-operated gas demand apparatus constructed according to a first embodiment of the present invention.

As generally introduced in FIG. 1, a pneumatically-operated gas demand apparatus 10 is coupled in interruptible fluid communication between a recipient 12 and at least one source 14 of pressurized respiratory gas such as oxygen. Conventional tubing 16 interconnects pneumatically-operated gas demand apparatus 10 to source 14 and a partitioned, nasal cannula assembly 18 interconnects pneumatically-operated gas demand apparatus 10 and recipient 12. A dual-lumen, nasal cannula assembly (not shown) can also be employed and is well known in the art and no additional explanation thereof is deemed necessary to practice the present invention. A first lumen 20 of a dual-lumen, nasal cannula assembly 18 is connected between pneumatically-operated gas demand apparatus 10 and recipient 12 to conduct oxygen to a nose 22 of the recipient. A second lumen 24 is connected between pneumatically-operated gas demand apparatus 10 and cannula 18 to act as a conduit so that inhalation pressure and exhalation pressure to and from recipient 12 can be conveyed to and from pneumatically-operated gas demand apparatus 10. As a result, pneumatically-operated gas demand apparatus 10 is adapted for controlling delivery of gaseous oxygen to recipient 12 as the recipient inhales and exhales.

Pneumatically-operated gas demand apparatus 10 comprises a supply valve 28 and a sensing valve 30 constructed substantially similarly to the supply and sensing valves of the pneumatically-operated gas demand apparatus disclosed in U.S. Pat. No. 5,666,945 to Davenport. The details of such valves will be generally described but not illustrated herein because they do not, per se, form a part of the present invention and are believed to be understood by those of ordinary skill in the subject art. More particularly, supply valve 28 includes a supply valve housing and a flexible first diaphragm member. The supply valve housing defines a first interior chamber which is formed therein. A flexible first diaphragm member is disposed within the first interior chamber and is connected to the supply valve housing in a manner to divide the first interior chamber into a supply chamber region and a control chamber region. The supply chamber region is in interruptible fluid communication with and between source 14 of the pressurized oxygen and recipient 12. Throughout the description of the exemplary embodiments, the phrase, "interruptible fluid communication" is used and, by way of example only, "interruptible fluid communication" means that sometimes the supply chamber region is in fluid communication with source 14 while at other times the supply chamber region is not in fluid communication with source 14. The control chamber region is in continuous fluid communication with source 14 of pressurized oxygen. The first diaphragm member is operative to hermetically seal the supply chamber region and the control chamber region from one another. Additionally, the first diaphragm member is operative to move between a flow-blocking position and a flow-supplying position when the recipient exhales and inhales, respectively.

The sensing valve includes a sensing valve housing and a flexible second diaphragm member. The sensing valve housing defines a second interior chamber which is formed therein. The second diaphragm member is disposed within second interior chamber and is connected to the sensing valve housing in a manner to divide the second interior chamber into a venting chamber region and a sensing chamber region. The venting chamber region is in interruptible fluid communication with and between the control chamber region of the first interior chamber of supply valve 28 and an ambient air environment through a bleed conduit. The sensing chamber region is in continuous fluid communication with recipient 12.

The second diaphragm member is operative to hermetically seal the venting chamber region and sensing chamber region from one another. Further, the second diaphragm member is responsive when recipient 12 inhales and exhales by moving between a flow-stopping position and a flow-causing position. When recipient 12 inhales, the second diaphragm member is in the flow-causing position thereby causing oxygen to flow from the control chamber region, through the venting chamber region and into the ambient air environment through the bleed conduit. In turn, the second diaphragm member being in the flow-causing position causes the first diaphragm member to be in the flow-supplying position thereby delivering oxygen from source 14 of pressurized oxygen to recipient 12. When recipient 12 exhales, the second diaphragm member is in the flow-stopping position thereby preventing oxygen to flow from the control chamber region, through the venting chamber region and into ambient air environment which, in turn, causes the first diaphragm member to be in the flow-blocking position thereby preventing delivery of oxygen to recipient 12. The supply and sensing valves 28, 30 further preferably include suitable springs for yieldably urging the first diaphragm member into the flow-supplying position and the second diaphragm into the flow-stopping position, respectively. The sensing valve further preferably includes means such as a set screw or the like for adjusting the seating force exerted by the sensing valve spring against the second diaphragm member such that the recipient may easily unseat the second diaphragm member and enable oxygen flow past the first diaphragm during inhalation.

When the source 14 of respiratory gas is a pressurized cylinder of oxygen, nitrous oxide or the like, the respiratory gas is typically discharged at a pressure of between about 200–3000 psi, which pressure may be detected on a conventional pressure gauge 32 connected to tubing 16. Apparatus 10 further includes, depending on its intended use or application, a regulator mechanism comprising one or more pressure regulators for controlling the pressure and flow rate of respiratory gas delivered by the apparatus to recipient 12. When configured to administer respiratory gas from a highly pressurized source 14, the regulator mechanism of apparatus 10 preferably comprises an internal (as illustrated) or external high pressure regulator 34 for reducing the gas pressure from source 14 about 50–60 psi. The system further preferably includes a suitable relief valve 36 such as a check valve, poppet valve or the like, operable to release excess gas pressure about above 75 psi in the event of failure of the high pressure regulator 34, which pressure might otherwise cause malfunction and/or damage to apparatus 10.

According to all contemplated embodiments of the present invention, the regulator mechanism of apparatus 10 includes a low pressure regulator 38. Low pressure regulator 38 preferably functions in a range of about 10–40 psi and is operable to be used in conjunction with high pressure regulator 34, as shown, when the source 14 of respiratory gas is highly pressurized, or by itself when the source 14 is liquid oxygen or an air compressor. For example, when apparatus 10 is used to power a nebulizer on demand, i.e., only during the early stages of inhalation, source 14 would likely be a comparatively low pressure air compressor.

Apparatus 10 further preferably includes a multiple function flow rate selector means 40. According to a presently preferred construction, flow rate selector means 40 comprises a rotatable member for controlling gas flow to the low pressure regulator 38 and gas flow from one bolus chamber to another bolus chamber or the recipient 12 in the manner described below. The flow rate selector means 40 preferably includes first flow control means 42 that is disposable into a CLOSED position whereby gas flow to the low pressure regulator 38 and the recipient 12 is shut off. When in a range of OPEN positions, the first flow control means 42 is operable to deliver pressurized gas flow in a desired range, for example, about 0.5–6 l pm, to the low pressure regulator 38.

From the low pressure regulator 38 gas flow is communicated through a first passageway 44 to a bolus chamber 46 and through a second passageway 48 to another bolus chamber 50. Bolus chambers 46 and 50 distribute the recipient demand flow requirements of apparatus 10 in such a way that wide ranges of demand flow may be accommodated by the apparatus without detrimentally affecting its performance. Passageways 44, 48 split the gas flow to the bolus chambers 46, 50 such that neither bolus chamber operates under a pressure range that could deleteriously impact operation of the apparatus. More specifically, first passageway 44 is provided with a fixed or, more preferably, an adjustable, variable orifice type supply orifice element 52 of conventional construction which is operable to deliver gas flow at a rate of about 1.5 to about 4.5 l pm to bolus chamber 46. Accordingly, the pressure range of bolus chamber 46 is about 3:1 (i.e., which causes a flow ratio of approximately 4.5 l pm/1.5 l pm). Similarly, passageway 48 is provided with a conventional fixed or, more preferably, an adjustable, variable orifice type supply orifice element 54 operable to deliver gas flow at a rate of about 0.5 to about 1.5 l pm to bolus chamber 50. Hence, the pressure range of bolus chamber 50 is also about 3:1 (i.e., which causes a flow ratio of approximately 1.5 l pm/ 0.5 l pm).

Apparatus 10 also desirably includes a conventional fixed or, more preferably, an adjustable, variable orifice type sensing or pilot orifice element 56. The pilot orifice element 56 is disposed in a passageway 58 between the first control means 42 and the control chamber region of the supply valve 28. Since the control chamber region of the supply valve 28 is in fluid communication with the sensing valve 30 during inhalation, FIG. 1 depicts an inspiration phase whereby the pilot orifice element communicates with sensing valve 30. When the first flow control means 42 of flow rate selector means 40 is in the OPEN position, pilot orifice element 56 may deliver a flow of up to about 0.2 l pm of pressurized respiratory gas to the supply valve 28, which flow is communicated to the sensing valve 30 during inspiration. Passageway 58 may also include a continuous flow selector 60 if the pilot orifice element 56 is of the fixed-flow variety.

In addition to the first flow control means 42, flow rate selector means 40 also preferably comprises a second flow control means 62 that is disposable into a CLOSED position whereby gas flow from bolus chamber 46 is shut off and the only flow delivered by apparatus 10 to supply valve 28 is that conveyed by passageway 48 to bolus chamber 50. Thus, when the recipient 12 inhales, he or she receives a comparatively low-level bolus of respiratory gas from bolus chamber 50 at the onset of inhalation followed thereafter by a continuous flow of between about 0.5–1.5 l pm flow of respiratory gas for the remainder of the inspiratory phase. Such low bolus discharge and flow rates may be desirable, for example, to conserve oxygen during use by sedentary persons.

When the second flow control means 62 is in the OPEN position and the recipient 12 inhales, at the onset of inhalation the recipient receives through supply valve 28 the combined boluses from bolus chambers 46 and 50. Thereafter the recipient receives the combined flows conveyed by passageways 44 and 46 (i.e., about 2–6 l pm) for the remainder of the inhalation phase. The bolus chambers 46, 50 may be connected in series or parallel relationship. That is, apparatus 10 may be configured such that bolus chamber 46 discharges either into bolus chamber 50 or directly into supply valve 28, the latter being indicated by dot-dash line 64.

The pneumatically-operated gas demand apparatus 10 of the present invention can minimize wastage of oxygen. The pneumatically-operated gas demand apparatus delivers a high-flow pulse of oxygen to the recipient/patient during an initiation period of the recipient/patient's inhalation phase of the breathing cycle. This high-flow pulse of oxygen causes oxygen enrichment of the exhaled air remaining in a nasal and other portions of the respiratory passageway from the prior exhalation phase of the breathing cycle. With this enriched exhaled air now becoming the first air to be inhaled into the recipient's lungs, more therapeutically valuable oxygen can be utilized by the recipient. Thereafter, a continuous flow of oxygen is delivered to the recipient throughout the remaining period of inhalation phase of the breathing cycle. As described, the pneumatically-operated gas demand apparatus can be fabricated from readily available components or can be integrated into a unitary construction. In either regard, the pneumatically-operated gas demand apparatus is simple in design and compact.

Distributing a typical demand flow range of about 0.5–6 l pm among several bolus chambers produces several advantages over systems involving a single bolus chamber. First, the pressure ranges may be significantly reduced, e.g., from as much as about 12:1 or more for a single bolus chamber design to about 3:1 for each chamber of a double bolus chamber design. The significantly reduced pressure ranges for each of the multiple bolus chambers effectively combine to eliminate dynamic performance problems in both the supply and sensing valves. Additionally, the low pressure regulator 38 may be selected to have a relatively restrictive operating range (e.g., about 10–40 psi) whereby errors in the operation of the low pressure regulator are avoided, even at low flow system settings.

Figure 2:
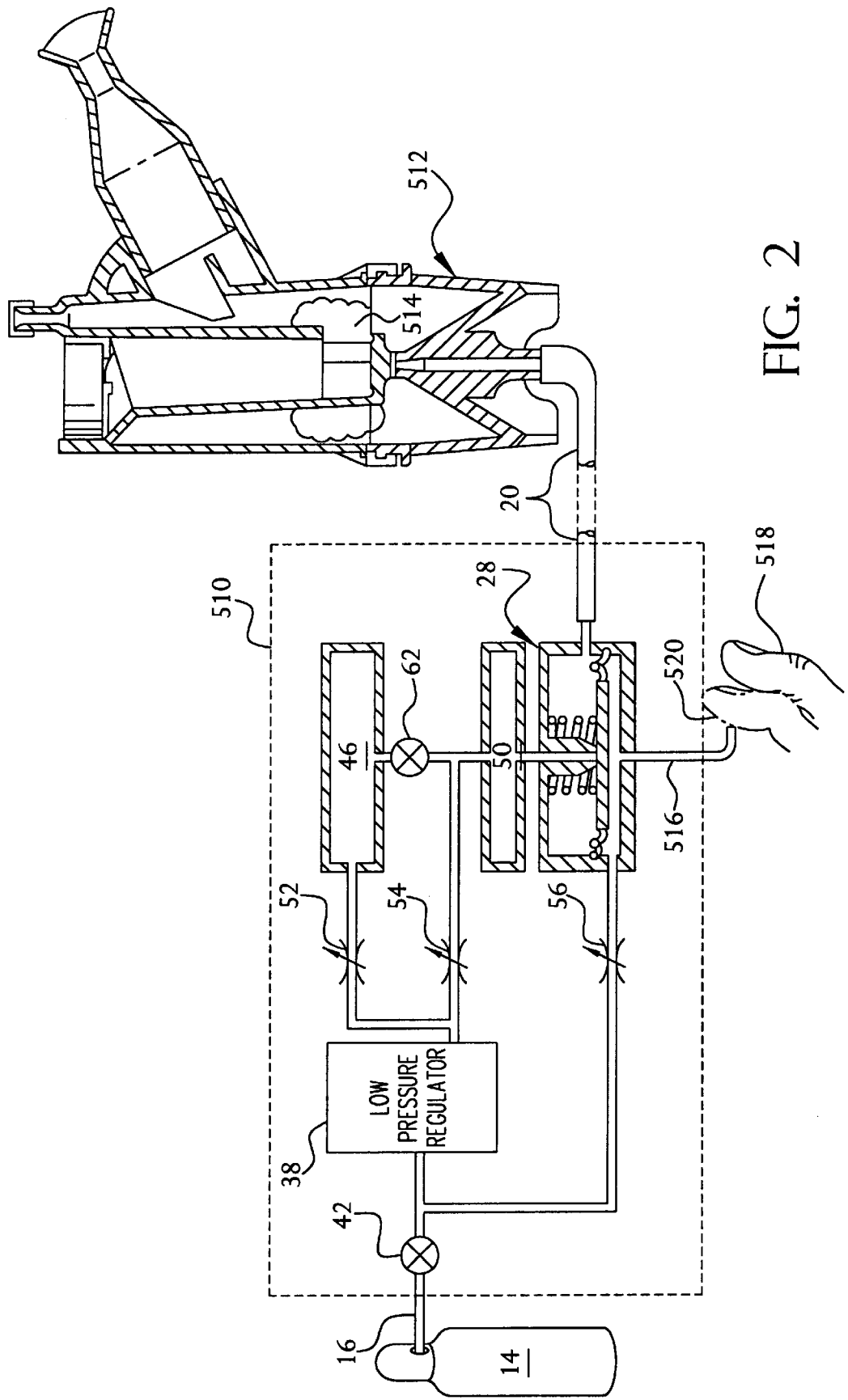
FIG. 2 is a partial schematic and partial cross sectional view of a further embodiment of the present invention constructed as an intermittent gas delivery device used in combination with a conventional nebulizer.

As shown in FIG. 2, it is also contemplated that apparatus 10 can be combined to construct an intermittent gas delivery device 510 generally similar to that described in U.S. Pat. No. 5,666,945. Such intermittent gas delivery device could be utilized, for example, with a nebulizer such as the one described in U.S. Pat. No. 5,584,285 to Chua, et al. Other nebulizers are commonly known in the art and can be employed with the present invention if equipped with an inhalation sensing structure or supplemental sensing apparatus. With intermittent gas delivery device 510 connected in fluid communication between source 14 of pressurized gas, such as air or oxygen, and a nebulizer 512, intermittent gas delivery device 510 generates a fine-mist plume 514 of a medicament-containing aerosol by first permitting the pressurized gas into nebulizer 512. Initially, a high flow pulse of the pressurized gas from the multiple bolus chambers 46, 50 generates this fine-mist plume and subsequently a steady state flow of the gas delivered to nebulizer 512 continues to generate and deliver this fine-mist plume to the patient. The high flow pulse and subsequent steady flow sequentially occurs by the implementation of a sense tube 516. A finger 518 of the recipient being placed over a sense tube inlet 520 causes supply valve 28 to be in the flow-blocking position. Removing finger 518 from sense tube inlet 520 causes supply valve 28 to move to the flow-supplying position. One of ordinary skill in the art would appreciate that other methods such as mechanically triggering supply valve 28 during a selected interval of time within each breathing cycle could be utilized in lieu thereof.

Although the invention has been described in detail for the purpose of illustration, it is to be understood that such detail is solely for the purpose and that variations can be made therein by those skilled in the art without departing from the spirit and scope of the invention except as it may be limited by the claims.

What is claimed is:

1. A pneumatically-operated gas demand apparatus coupled in interruptible fluid communication between a recipient and at least one source of a pressurized gas and adapted for controlling delivery of the pressurized gas to the recipient as the recipient inhales and exhales, comprising:

a supply valve and a sensing valve;

said supply valve being in communication with the at least one pressurized gas source, said sensing valve and the recipient, said supply valve being operable to move between a flow-supplying position and a flow-blocking position responsive to movement of said sensing valve;

said sensing valve being in communication with the at least one pressurized gas source, said supply valve and the recipient, said sensing valve being operable to move between a flow-stopping position whereby said supply valve assumes said flow-blocking position when the recipient exhales thereby preventing delivery of the gas to the recipient and a flow-causing position whereby said supply valve assumes said flow-supplying position when the recipient inhales thereby delivering the gas from the pressurized gas source to the recipient;

a regulator mechanism including at least one regulator disposed between and in interruptible fluid communication the pressurized gas source and said supply valve; and a plurality of bolus chambers disposed between and in fluid communication with said at least one regulator and said supply valve, said plurality of bolus chambers comprising a bolus chamber adapted to accommodate a portion of pressurized gas flow delivered from said at least one regulator, and at least one additional bolus chamber adapted to accommodate at least one additional portion of pressurized gas flow delivered from said at least one regulator.

2. The apparatus of claim 1 wherein said bolus chamber and said at least one additional bolus chamber are connected in series.

3. The apparatus of claim 1 wherein said bolus chamber and said at least one additional bolus chamber are connected in parallel.

4. The apparatus of claim 1 further comprising:

a supply orifice element having a supply orifice formed therethrough, said supply orifice element being disposed and providing fluid communication between said at least one regulator and said bolus chamber; and at least one additional supply orifice element having a supply orifice formed therethrough, said at least one additional supply orifice element being disposed and providing fluid communication between said at least one regulator and said at least one additional bolus chamber.

5. The apparatus of claim 1 wherein said portion of pressurized gas flow and said at least one additional portion of pressurized gas flow are unequal.

6. The apparatus of claim 1 wherein the ratio of maximum gas flow rate to minimum gas flow rate accommodated by said bolus chamber is about 3:1.

7. The apparatus of claim 1 wherein the ratio of maximum gas flow rate to minimum gas flow rate accommodated by said at least one additional bolus chamber is about 3:1.

8. The apparatus of claim 1 wherein the total gas flow rate accommodated by said bolus chamber and said at least one additional bolus chamber is about 0.5 to about 6 liters per minute.

9. The apparatus of claim 1 further comprising flow rate selector means for controlling flow of pressurized between the at least one pressurized gas source and said supply valve, said flow rate selector means including first flow control means for controlling pressurized gas flow from the at least one pressurized gas source and said at least one regulator and second flow control means for controlling pressurized gas flow from said plurality of bolus chambers to said supply valve.

10. In combination with a nebulizer for producing a medicament-containing aerosol and a source of pressurized gas, an intermittent gas delivery device disposed between and in intermittent fluid communication with the nebulizer and the source of pressurized gas, comprising:

a regulator mechanism in continuous fluid communication with and disposed downstream of the pressurized gas source;

a plurality of bolus chambers disposed downstream of and in fluid communication with said regulator mechanism, said plurality of bolus chambers comprising a bolus chamber adapted to accommodate a portion of pressurized gas flow delivered from said at least one regulator, and at least one additional bolus chamber adapted to accommodate at least one additional portion of pressurized gas flow delivered from said at least one regulator;

a plurality of supply orifices disposed and providing fluid communication between said regulator mechanism and said plurality of bolus chambers, each of said plurality of supply orifices providing fluid communication between said regulator mechanism and a respective one of said bolus chambers; and a supply valve in downstream fluid communication with said plurality of supply orifices and operative to move between a flow-blocking position whereby the pressurized gas is prevented from flowing from the pressurized gas source to the nebulizer and a flow-supplying position whereby the pressurized gas flows from the pressurized gas source to the nebulizer such that a high flow pulse of pressurized gas first generates a fine-mist plume of the medicament-containing aerosol in the nebulizer and subsequently a steady state flow of pressurized gas continues to produce the fine-mist plume of the medicament-containing aerosol in the nebulizer until said supply valve moves to the flow-blocking position.

11. An intermittent gas delivery device according to claim 10 including a sense tube connected in fluid communication with said supply valve and having a sense tube inlet thereinto, said sense tube operative with a finger of the recipient to be placed over said sense tube inlet to cause said supply valve to be in the flow-blocking position and to be removed from said sense tube inlet to cause said supply valve to move to the flow-supplying position.

* * * * *